(12) United States Patent
Gordon (10) Patent No.: US 9,549,753 B2
(45) Date of Patent: Jan. 24, 2017

(54) FLUID JET CELL HARVESTER AND CELLULAR DELIVERY SYSTEM

(76) Inventor: Christopher Burnside Gordon, Cincinnati, OH (US)

(*) Notice: Subject to any disclaimer, the term of this patent is extended or adjusted under 35 U.S.C. 154(b) by 402 days.

(21) Appl. No.: 14/009,198

(22) PCT Filed: Mar. 31, 2012

(86) PCT No.: PCT/US2012/031747
§ 371 (c)(1),
(2), (4) Date: Oct. 1, 2013

(87) PCT Pub. No.: WO2012/135794
PCT Pub. Date: Oct. 4, 2012

(65) Prior Publication Data
US 2014/0058361 A1 Feb. 27, 2014

Related U.S. Application Data

(60) Provisional application No. 61/470,722, filed on Apr. 1, 2011.

(51) Int. Cl.
*A61B 17/3203* (2006.01)
*A61M 1/00* (2006.01)
(Continued)

(52) U.S. Cl.
CPC ........ *A61B 17/3203* (2013.01); *A61M 1/0031* (2013.01); *A61B 17/320068* (2013.01);
(Continued)

(58) Field of Classification Search
CPC ................. A61B 17/3203; A61B 2017/00154; A61B 2217/005; A61B 17/22004; A61B 2017/22005; A61B 2017/22007; A61B 2017/22008; A61B 2017/22011; A61B 2017/32032; A61B 2017/1648; A61B 17/1644; A61B 17/320068; A61B 2017/32008; A61B 2017/320084; A61M 1/0031; B05B 17/063; B05B 17/0623; B08B 2203/0288; B08B 3/12; B26F 2003/006; B24C 5/005; B24C 5/02; B24C 5/04
See application file for complete search history.

(56) References Cited

U.S. PATENT DOCUMENTS 3,522,801 A * 8/1970 Robinson ............... A61C 17/20
433/119
4,391,281 A 7/1983 Green
(Continued)

OTHER PUBLICATIONS

Extended European Search Report (EESR) for European Application No. 12763482.2 dated Dec. 12, 2014, (8 pages).
(Continued)

*Primary Examiner* — Adam Marcetich
(74) *Attorney, Agent, or Firm* — Tucker Ellis, LLP (57) ABSTRACT

An ultrasonically pulsating high-pressure fluid jet coupled with a suction system serve as a tissue harvesting device. The pulsated fluid jet disrupts tissue, permitting both harvesting of cells for therapeutic delivery, and as a surgical dissector and aspirator, for liposuction, soft tissue dissection, etc. The jet is delivered to the target tissue through a cannula, coupled to an aspiration system. An ultrasonically actuated rod vibrates within the cannula engaging a nozzle, disrupting the fluid jet into droplets, permitting tuning of the jet to the resonant frequencies and impact pressures necessary to dissociate the target tissue. A suction recovery system may be separated or integrally formed with the fluid jet cannula, and is linked by a closed tubing system appropriate for sterilization and subsequent delivery of the harvested cells/tissues with or without growth factor or matrix addition for human re-implantation or for in vitro expansion for later re-implantation.

52 Claims, 6 Drawing Sheets

(51) Int. Cl.
  *A61B 17/32* (2006.01)
  *B05B 17/06* (2006.01)
  *B24C 5/00* (2006.01)
  *A61B 17/00* (2006.01)

(52) U.S. Cl.
  CPC .............. *A61B 2017/00154* (2013.01); *A61B 2017/320084* (2013.01); *A61B 2217/005* (2013.01); *B05B 17/063* (2013.01); *B08B 2203/0288* (2013.01); *B24C 5/005* (2013.01)

(56) References Cited

U.S. PATENT DOCUMENTS

| | | | | |
|---|---|---|---|---|
| 4,930,700 | A * | 6/1990 | McKown | B05B 17/0623 239/102.2 |
| 5,112,300 | A * | 5/1992 | Ureche | A61F 9/00745 310/323.18 |
| 5,170,989 | A * | 12/1992 | Kemp | F16K 5/0668 251/174 |
| 5,494,258 | A * | 2/1996 | Weissgerber | F04B 53/108 251/129.17 |
| 5,496,267 | A | 3/1996 | Drasler et al. | |
| 5,591,184 | A | 1/1997 | McDonnell et al. | |
| 5,875,922 | A * | 3/1999 | Chastine | B05C 5/02 222/1 |
| 5,927,329 | A * | 7/1999 | Yie | A62C 31/02 137/624.13 |
| 6,013,048 | A | 1/2000 | Podany et al. | |
| 7,063,713 | B1 | 6/2006 | Butsch et al. | |
| 2002/0138036 | A1* | 9/2002 | Babaev | A61B 17/22 604/22 |
| 2003/0105422 | A1* | 6/2003 | Gonon | A61B 17/32037 604/21 |
| 2003/0167053 | A1* | 9/2003 | Taufig | A61M 1/0084 604/542 |
| 2005/0159765 | A1 | 7/2005 | Moutafis et al. | |
| 2007/0063066 | A1* | 3/2007 | Vijay | B26F 3/004 239/99 |
| 2008/0132888 | A1 | 6/2008 | Iida et al. | |
| 2008/0132889 | A1 | 6/2008 | Wakamatsu et al. | |
| 2008/0300611 | A1 | 12/2008 | Houser et al. | |
| 2009/0306694 | A1 | 12/2009 | Babaev | |
| 2009/0308948 | A1 | 12/2009 | Vijay et al. | |
| 2009/0318944 | A1* | 12/2009 | Kimura | A61B 17/16 606/169 |
| 2010/0036388 | A1* | 2/2010 | Gomez | A61F 9/00745 606/107 |
| 2010/0082053 | A1 | 4/2010 | Hama et al. | |
| 2010/0191173 | A1 | 7/2010 | Kimura et al. | |
| 2010/0279405 | A1 | 11/2010 | Peterson et al. | |
| 2010/0280435 | A1* | 11/2010 | Raney | A61M 1/0031 604/22 |
| 2010/0296975 | A1* | 11/2010 | Peshkovsky | B01J 19/008 422/128 |
| 2012/0322347 | A1* | 12/2012 | Molz | B05B 1/08 451/40 |

OTHER PUBLICATIONS

International Search report for PCT/US12/31747 dated Jul. 24, 2012, 2 pp.

* cited by examiner

FLUID JET CELL HARVESTER AND CELLULAR DELIVERY SYSTEM

CROSS REFERENCE TO RELATED APPLICATIONS

This application is based on and claims priority to International Application No. PCT/US12/31747, having the International filing date of Mar. 31, 2012, the disclosure of which is included herein by reference in its entirety, which claims priority to U.S. provisional patent application Ser. No. 61/470,722 filed Apr. 1, 2011, the disclosure of which is included herein by reference in its entirety.

BACKGROUND OF THE INVENTION

1) Technical Field

Embodiments herein relate to systems for generating pulsating liquid jets directed at a workpiece and for removal of material from the workpiece in areas thereof impacted by the pulsating liquid jet. Particular embodiments herein relate to fluid jet surgical devices and more specifically to ultrasonically pulsated fluid jet surgical devices for enhanced tissue harvesting suitable for both ablative therapy and for collection of cellular materials such as for regenerative medicine or other purposes.

2) Background Art

The use of basic fluid jets in surgery is well known in the art. These devices can be generally divided into two categories of continuous and pulsated jets. Examples of prior art disclosing continuous jets include U.S. Pat. No. 6,375,635 (Moutafis).

Examples of previously disclosed devices include U.S. Pat. Nos. 3,818,913 and 3,930,505 (Wallach) interrupted jet, does not specify method for interrupting, European Patent EP 0636345 Sentinel Medical, and World Patents Surgical instrument with interrupted stream created by piston pump. Gonon—Interrupted fluid jet utilizing periodic interruption of stream alternating with suction with fluid delivery. WO-2006-026969 Pein and Tork—Continuous water jet with fan shaped pattern and integrated liposuction. WO/2008/074284 Kensy, Winkler et al—Continuous water jet with clear chamber to permit wound care without spray of material. Puchala, R. J. and Vijay, M M, Study of an ultrasonically Generated Cavitating or Interrupted Jet: Aspects of Design, Paper B2, Proceedings of the 7th International Symposium on Jet Cutting Technology, Paper B2: 69-82, 1984. Vijay, M M, Foldyna J, Remisz J, 1993.

Continuous flow water jets have several disadvantages. First, they rely upon stagnation pressure or erosive pressure of the fluid stream. The skilled practitioner will recognize that this leads to inefficient tissue disruption, the need for high pressures to effect tissue disruption, and potential unintended injury to tissues in the path of the fluid jet. Additionally, this additional pressure results in widespread cellular injury, rendering the aspirate unsuitable for use in regenerative medicine as a source of viable cells and tissue for engraftment. Examples of this approach include ((Moutafis)) which relies upon the delivery of a continuous fluid jet into the orifice of a suction tube. In order to ablate tissue, the stream is passed tangentially across the desired tissue, and suction draws the target tissue into the stream. The skilled practitioner will further recognize that devices of this design are bulky, relatively inefficient at tissue ablation, and unsuited to many types of surgery.

Later devices introduced interrupted fluid streams which were more efficient at tissue ablation. These devices have relied upon periodic interruption of a fluid jet to increase tissue destruction. The speed with which the fluid stream can be interrupted with mechanical devices is limited, however, resulting in inefficient droplet or slug formation, and permitting only an incremental increase in efficiency of tissue harvest. Further, at the frequencies and volumes attainable with these types of devices, the practitioner will recognize that tissue-specific tailoring of the frequency of the pulsation is unattainable.

Hansell, June 1950, disclosed a Jet Sprayer actuated by supersonic waves which relied upon but this device was generally unsuccessful.

Current technology for transplanting mesenchymal stem cells (MSCs) for cellular therapy utilizes conventional liposuction. Adipose tissue has thousands of fold more MSCs than other mesenchymally derived tissues. These cells are present in all adipose tissue, and can be used for reinjection either with or without further manipulation, culture, growth factors, etc, to regenerate tissues.

BRIEF SUMMARY

The embodiments herein relate to systems generating ultrasonically pulsated liquid jets and a suction at sites impacted by the pulsated liquid jets, wherein the systems herein have improved tissue disruption and harvesting capabilities. Further embodiments herein relate to methods of using systems generating ultrasonically pulsated liquid jets and a suction at sites impacted by the pulsated liquid jets for various purposes including for collection of cellular materials such as for regenerative medicine or other purposes and/or applications.

The device of the current example embodiment relies upon the relative incompressibility of water to deliver a percussive stream of droplets to dissociate the target tissue. Whereas previous devices simply disrupt the fluid stream, the current example embodiment utilizes an ultrasonic actuator to both interrupt a fluid stream and establish waves of ultrapressurization and depressurization within a fluid filled column. This pulsating stream stores energy in the droplets and delivers this energy to the target tissue upon impact, resulting in a "water hammer" effect that more efficiently dissociates tissue. In an embodiment the ultrasonic actuator is an elongate acoustic horn member formed of a suitable material such as titanium for example.

The concept is analogous to the military technology of using depleted uranium projectiles to literally vibrate enemy tanks to pieces. An interrupted or pulsated fluid jet stores energy in the surface tension of the droplets and delivers it to the substrate with a "hammer pressure" which is nearly 10 times that of a continuous stream fluid jet. In the example embodiment, this pulse frequency is selectively tuned to the resonant frequency of the target tissue resulting in selective dissociation. For example, the jet can be tuned to the resonant frequency of fat (approximately 22-27 kHz), resulting in highly efficient emulsification of mature adipose tissue, and release of a variety of cell types in the effluent. This dissociation is selectively advantageously enhanced by pulsating the stream at different frequencies and pressures to tune the pulsated stream to match the properties of the target tissue. This efficient emulsification of mature adipose tissue, and release of a variety of cell types in the effluent can be aspirated at the point of impact (integrated cannula), or subsequently aspirated using conventional liposuction.

In the example embodiment, the tuned nozzle has a taper representing an integral number of half wave lengths ($L=n\lambda/2$) to the ultrasonic frequency. In the embodiment, the nozzle, the tip portion of the vibrating probe, and the water chamber defined within the handpiece are sized and formed for enhanced harmonics matching of the components collectively in accordance with the operational ultrasonic frequency of the device for enhanced manipulation of the pulsated fluid jet for effecting the desired results relative to the associated tissue workpiece.

When used to disrupt adipose tissue, the effluent advantageously consists of a large volume of acellular lipid, a small number of adipocytes in a separate layer, and an aqueous fraction containing a large number of mixed mesenchymal stem cells (MSCs), vascular cells, fibroblasts, immune cells, and other cell types which are beneficial to the reengraftment of the MSCs for tissue regeneration. This effluent naturally settles into three layers, permitting selection of the aqueous fraction as a stem-cell rich cellular concentrate which is suitable for transplantation. Additionally, the effluent has a very thin consistency which is easier to aspirate than with traditional liposuction.

The system of the embodiments herein serve at least two purposes. First, it efficiently harvests adipose-derived MSCs from subcutaneous tissues and concentrates them along with supporting cells that aid tissue regeneration in a single procedure, obviating the need for subsequent digestion, elution, centrifugation or manipulation. Second, it is a highly efficient liposuction device and can be used as a soft tissue dissector in other surgical disciplines. Other purposes and advantages will occur to those skilled in the art after reading and understanding the descriptions herein.

Background art in the adipose-derived MSC field is dependent upon the conventional liposuction approach followed by elution/digestion or dissociation. The approach of the subject example embodiments has multiple clinical advantages. First, the device results in a very efficient in situ concentration of target cells, permitting rapid reinfusion or replantation. Second, it avoids time consuming post-harvest processing. Third, from a regulatory standpoint, it will likely avoid PMA requirements and reach market via the 510k pathway. Finally, it has utility in other surgical markets, such as aesthetic surgery (liposuction), and bone or solid organ surgery as an alternative to existing harmonic or water jet technology. Further advantages include recurrent disposable sales, early entry into stem cell transplantation arena, synergy with growth factors, and applicability to orthopedic surgery (non-union, etc.).

In one embodiment, the system comprises a high pressure fluid source, a handpiece/cannula containing the ultrasonic valve through which the fluid is delivered to the tissue as an ultrasonically pulsated fluid jet, and a suction system to recover the dissociated tissue. The fluid source is preferentially an electric pump capable of delivering high pressure in the circuit. In a preferred embodiment, the pump comprises a piston reduction system with a disposable fluid circuit. This permits the transfer of the pumping pressures across a sterile diaphragm to transmit hydraulic pressure from the non-sterile pump side of the circuit to the sterile fluid of the fluid jet circuit. The suction system preferentially comprises a vacuum canister coupled with a cannula via a hose wherein the cannula at a working tip of the system adjacent the associated tissue for drawing disassociated or ablated tissue from the area impacted by the pulsated fluid jet and into the vacuum canister for collection and selective separation or any other further processing as necessary or desired.

In a preferred embodiment, the fluid jet handpiece consists of ultrasonic actuator, which is attached to one end of an ultrasonic transducer apparatus including on the other end an acoustic horn member comprising a titanium rod with a conical. tip. This rod engages a seat, wherein the horn and seat collectively form a needle valve. This valve seat is attached to an elongate thin capillary or tube to deliver the fluid stream to the target tissue. Additionally, a distal portion of the capillary or the entire capillary can be contained within a cannula through which the disrupted tissue can be aspirated for collection and disposal or sterile delivery for regenerative medicine. The needle tip advances and interrupts the stream by entering the nozzle with each ultrasonic cycle, resulting in generation of a pulsed stream. The fluid velocity, droplet size and frequency are controlled by the inlet pressure/nozzle size and length of ultrasonic cycle, and ultrasonic generator frequency respectively. A control unit is integrated into the handpiece that permits opening and closing the high-pressure circuit and engaging the ultrasonic actuator. This fluid jet cannula may be enclosed within a suction cannula or the suction may be performed with a disposable cannula. The suction aspirator may be controlled at the handpiece or off-board, if performed with a separate suction system. Overall, the ultrasonic transducer apparatus vibrates relative to the handpiece on a node portion thereof formed between the acoustic horn end and the attachment end wherein the ode portion is sandwiched between opposed resilient members carried by the handpiece body.

The suction system to recover the dissociated tissue comprises an aspirator circuit consisting in the example embodiment of a surgical aspirator extending from the distal end of the pulse delivery tube apparatus, along a position thereof, and being attached to closed, sterile tubing with an in-line filter connected to a receptacle for catching the concentrated cells.

DETAILED DESCRIPTION OF THE EMBODIMENTS

Figure 1:
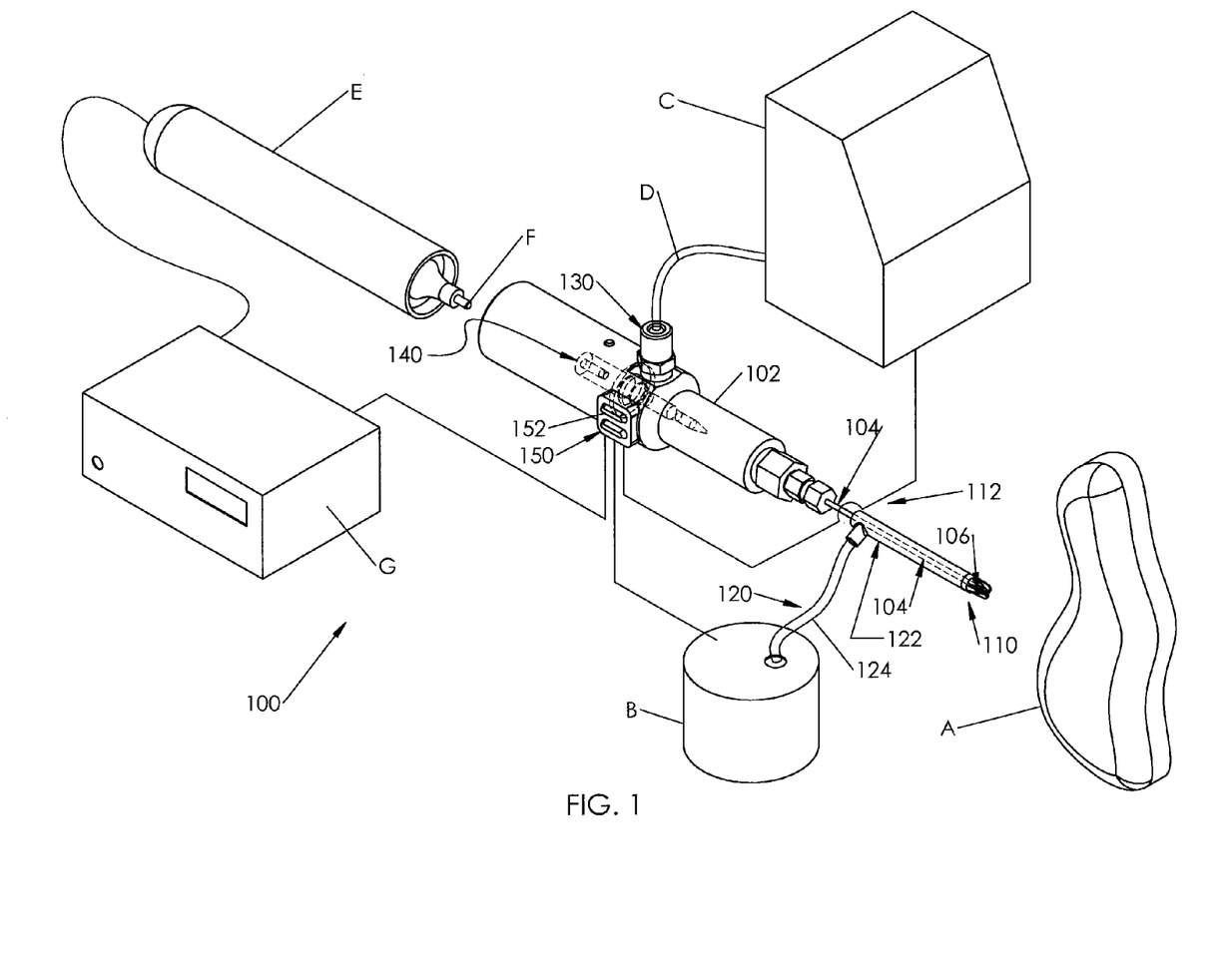
FIG. 1 is a schematic illustration of a system in accordance with an example embodiment.

With reference first to FIG. 1, a pulsated fluidjet system 100 in accordance with an example embodiment is shown in schematic form. The system 100 is configured in the example embodiment for ejecting a pulsated fluid stream at an associated workpiece A for workpiece ablation and/or dissemination and for harvesting ablated and/or disseminated portions of the workpiece. In the example embodiment, the workpiece is tissue such as human or animal tissue. However, it is to be appreciated that the workpiece may be any object or objects as necessary or desired. The system 100 of the example embodiment comprises a handpiece apparatus 102 and a delivery tube apparatus 104 for interfacing the handpiece apparatus 102 with the associated workpiece A. A working tip 106 of the delivery tube apparatus 104 is provided on a distal end 110 of the delivery tube apparatus 104 opposite the proximal end 112 thereof, wherein the proximal end 112 is coupled with the handpiece apparatus 102. In the example embodiment, the handpiece apparatus 102 is configured to generate a pulsated fluid stream and the delivery tube apparatus 104 is configured to communicate the pulsated fluid stream to the working tip 106 for impacting the associated workpiece A for selective workpiece ablation and/or dissemination.

The system 100 further comprises a suction aspirator apparatus 120 configured to harvest the ablated and/or disseminated portions of the associated workpiece A. In the example embodiment, the suction aspirator apparatus 120 comprises a cannula apparatus 122 extending from the working tip 106 along at least a portion of the delivery tube apparatus 104 and coupled with an associated collector device B such as a vacuum centrifuge or the like by an elongate flexible suction tube 124. In the ultrasonically actuated high-pressure waterjet surgical system of the example embodiment, the suction aspirator apparatus 120 interfaces with a closed loop tubing and vacuum transmission system to permit delivery of sterile collection of tissues and cells from the treated tissues. The suction aspirator selectively includes a filter element in a sterilizable container. Further in the example embodiment, the ultrasonic generator, aspirator and pump are selectively attached to a wheeled cart.

The handpiece apparatus 102 of the pulsated fluidjet system 100 of the example embodiment includes a first fluid port 130 configured to receive pressurized fluid from an associated pressure fluid source C via a suitable pressurized fluid conduit D. In the example embodiment, the pressurized fluid is sterile water.

In addition, handpiece apparatus 102 of the pulsated fluidjet system 100 of the example embodiment includes an ultrasonic transducer apparatus in the form of an elongate acoustic horn member 140 operatively coupled with an associated ultrasonic generator E via an associated connection member F of the associated ultrasonic generator E. The associated ultrasonic generator E is in turn coupled with an associated ultrasonic signal generator. G wherein the associated ultrasonic signal generator G is configured for delivery of high-frequency pulsed current to the associated ultrasonic generator E to convert electrical energy into ultrasonic vibrations by the associated ultrasonic generator E, which are in turn used to vibrate the ultrasonic transducer elongate acoustic horn member 140 via the associated connection member F for generating the pulsated fluid stream within the handpiece apparatus 102 using the pressurized fluid as the working medium and delivering the pulsated fluid stream to the working tip. In the example embodiment, The ultrasonic transducer of the subject ultrasonically actuated high-pressure waterjet system has an operational frequency of from about 15 kHz to about 60 kHz. Further in the example embodiment, the ultrasonic transducer has a frequency of about 27 kHz.

Overall, the handpiece apparatus 102 permits the conversion of electrical energy into ultrasonic vibrations at the probe portion or conical shaped tip of the acoustic horn 140 within the proximal end 112 of the cannula extending into the handpiece, interrupting the flow of the water jet as it exits the nozzle, delivering an ultrasonically pulsated or interrupted jet which is used for dissociation of the target tissue. The cannula 122 containing the probe comprising the delivery tube apparatus 104 therein can be introduced into a surgical wound, delivering a pulsed stream of fluid to the tissue, resulting in dissociation into cells, nonviable cellular debris, and an emulsion of tissue, permitting efficient aspiration for harvesting or removal. The associated pressurized fluid source C may be in the form of a closed-circuit which can be sterilized and attached to high pressure pump to permit delivery of high-pressure fluid to the nozzle and probe tip.

With continued reference to FIG. 1, the system 100 comprises, selectively, an electronic control unit 150 configured to generate plural control signals for selectively controlling the associated collector device B, the associated pressure fluid source C, and the associated ultrasonic signal generator G. The electronic control unit 150 includes a keypad 152 comprising suitable buttons, switches, or the like such as, for example, ON/OFF and a slide switches for selecting the operating frequency of the system 100 for permitting the operator of the subject pulsated fluidjet system 100 to control, using his hand, the action of the ultrasonic probe, the high pressure fluid source, and the suction device as necessary or desired to perform desired tasks relative to the workpiece. In an alternative embodiment, the electronic control unit 150 includes a footswitch (not shown) comprising suitable buttons, switches, or the like for permitting the operator of the subject pulsated fluidjet system 100 to control, using his foot, the action of the ultrasonic probe, the high pressure fluid source, and the suction device as necessary or desired to perform desired tasks relative to the workpiece.

In accordance with the example embodiment therefore, an ultrasonically pulsated waterjet surgical system 100 comprises a surgical handpiece apparatus including a port 130 for communication with an associated pressurized fluid source C and an ultrasonic transducer apparatus in the form of an elongate acoustic horn member 140 configured to generate ultrasonic vibrations within the handpiece apparatus 102 responsive to energy received from associated ultrasonic signal generator G and ultrasonic generator E members via an associated coupling member F. The frequency of the ultrasonic signal is preferably in the range of about 15 kHz to about 60 kHz. An operational frequency of about 27 kHz has been found to work particularly well, however. The system 100 further comprises a suction aspirator system 120 and an electronic control unit 150 for controlling the functions of the associated devices relative to the system 100. As noted, the electronic control unit 150 is disposed on the handpiece 102 but may be disposed at any convenient location such as, for example, in a footswitch control module, wall mounted module, or the like as necessary or desired.

Figure 2:
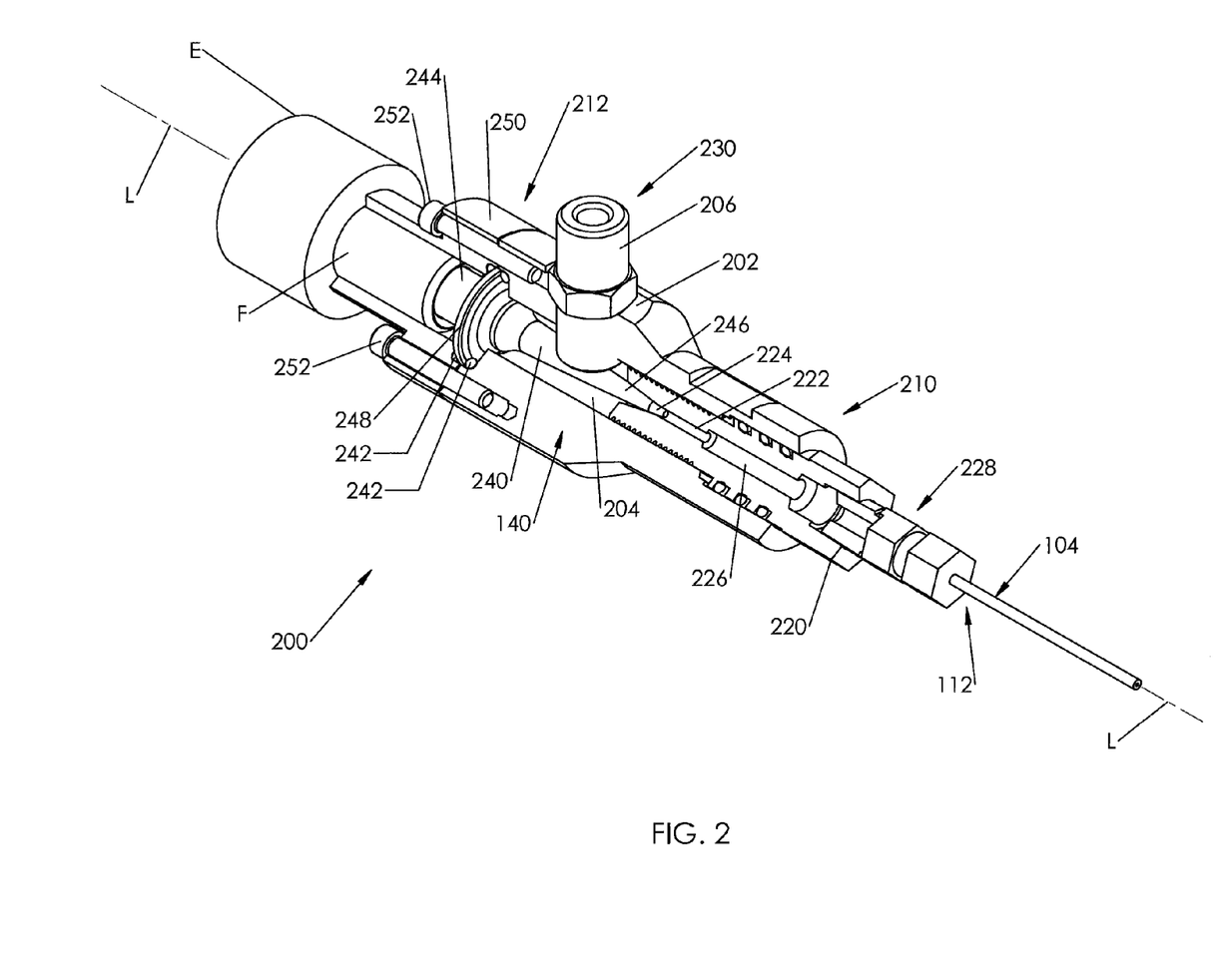
FIG. 2 is a perspective view of an embodiment of the handpiece apparatus of the subject system illustrated in partial cut-away view.

With reference to FIG. 2, an embodiment of a surgical handpiece apparatus 200 in accordance with a first example embodiment is shown in partial cut-away. The handpiece apparatus 200 of the example embodiment comprises an elongate substantially cylindrical hollow body member 202 defining a longitudinal passageway 204 therein. The passageway 204 is in fluid communication with a coupling member 206 forming a first fluid port 230 of the apparatus 200 and being configured to receive pressurized fluid from the associated source C (FIG. 1) via the associated pressurized fluid conduit D (FIG. 1).

A first or distal end 210 of the handpiece apparatus 200 is operatively coupled with the proximal end 112 of the delivery tube apparatus 104 via an intermediate coupling body 220 as shown. The intermediate coupling body 220 defines an elongate passageway 222 having a cone-shaped opening 224 defining a nozzle of the passageway 122 on one end and a long thin portion 226 on an opposite end, wherein the cone-shaped nozzle opening 224 is shaped to correspond with a portion of a vibrating piston member 240 in a manner to be described in greater detail below. The vibrating piston member 240 comprises, overall, an acoustic horn having an elongate probe on one end and directed at the nozzle 224 and functions in the embodiment as an ultrasonic transducer apparatus. The intermediate coupling body 220 may be selectively coupled with the hollow body member 202 using any suitable means including for example by providing selectively matable threads on opposite matable surfaces of the pieces and the intermediate coupling body 220 and hollow body member 202 may be provided with grooves or the like for carrying one or more seal members such a o-rings or the like for making the connection therebetween fluid tight. In the example embodiment, the delivery tube apparatus 104 is coupled with the body member by suitable pressure compression fittings 228.

A second or proximal end 212 of the handpiece apparatus 200 is operatively coupled with a substantially cylindrical clamping member 250 fastened to the hollow body member 202 using suitable longitudinally extending fasteners 252 such as socket head cap screws for example. The cylindrical clamping member 250 is configured to receive the associated connection member of the associated ultrasonic generator along the longitudinal axis thereof as illustrated for selective coupling with the ultrasonic acoustic horn apparatus 140 comprising the vibrating piston member 240 and a set of biasing members 242 in the form of o-rings in the example embodiment.

In accordance with the example embodiment, the acoustic horn member 240 functions as a piston member and defines a coupling end 244 configured for selective mechanical coupling with the associated connection member F and an opposite working tip portion 246. In that way, mechanical vibrational energy from the associated ultrasonic generator E causes the member 240 to vibrate along the longitudinal axis of the passageway 204 in turn forming pulses in the pressurized fluid within the passageway delivered from the port 230. The ultrasonic pulses are generated as the working tip portion 246 vibrates relative to the cone-shaped nozzle portion 224 of the intermediate coupling body 220. In turn, the ultrasonic pulses generated at the working tip portion 246 are directed into the delivery tube apparatus 104 for communication to the working tip 106 (FIG. 1) of the system 100 for impacting the associated tissue A or other workpiece. The nozzle is formed of any suitable material, but is in one embodiment formed of a titanium alloy. In another embodiment the nozzle is formed of ceramic, and in yet another embodiment it is formed of sapphire. Further, with regard to the mechanical vibrational energy from the associated ultrasonic generator, one preferred range of operational frequency is from about 15 kHz to about 60 kHz. However, an ultrasonic transducer frequency of about 27 kHz has been found to be particularly effective for workpieces comprising human or animal tissue.

In the ultrasonically actuated high-pressure waterjet surgical system 100 of the example embodiment, the probe 140 terminates in a conical tip on one end which corresponds to the shape of the nozzle, and wherein the probe is connected on the opposite end with the transducer by a threaded rod or similar connection as necessary or desired. In addition, the probe is connected with the transducer by an acoustic horn. The acoustic horn is in the example embodiment a solid member, but it may selectively be a hollow member with a stepped design (a two-stage horn). Further, the acoustic horn can be made of duralumin to increase transmutation ratio.

It is to be appreciated that the probe of the ultrasonically actuated high-pressure waterjet surgical system of the example embodiment 100 may be a straight rod or a stepped rod, or a cone. In one embodiment, the probe is made of titanium alloy. In a further embodiment, the probe is isolated from the diaphragm portion thereof with one or more O-ring seal(s) of sufficient hardness to form a watertight seal. The probe is subjected to ultrasonic waves by its attachment to the transducer, resulting in an intermittent interruption of the water jet. It is further to be appreciated that in the example, embodiment the nozzle orifice shape enhances the impact pressure of the interrupted fluid jet stream, wherein the nozzle is titanium alloy, ceramic, sapphire, or other materials having similar one or more properties.

Further in accordance with the example embodiment, the handpiece apparatus 200 may be selectively tuned by adjusting the relative position between the cylindrical clamping member 250 and the main body member 202, by adjusting the relative position between the intermediate coupling body 220 and the main body member 202, or by adjusting the relative positions of both the cylindrical clamping member 250 and the intermediate coupling body 220 relative to the main body member 202. More particularly, adjustments to the relative position between the cylindrical clamping member 250 and the main body member 202 control a clamping force exerted by the bias members 242 on an outwardly directed flange member 248 on the piston 240. As shown, in the example embodiment, the flange member 248 is sandwiched between the bias members 242 which are in turn held in opposed contact by the relative positions along the longitudinal axis L between the cylindrical clamping member 250 and the main body member 202. An amount of clamping force on the flange member 248 is used to control an amount of vibrational movement attained by the piston 240 when motivated by the associated ultrasonic generator E. Adjustments to the relative position between the cylindrical clamping member 250 and the main body member 202 may be made by selectively tightening and/or loosening the fastening members 252. The flange member 248 held in the manner described permits the acoustic horn member 240 to float in the water chamber 204 wherein the member 240 is thereby supported at an acoustic node thereof. In the example ultrasonically actuated high-pressure waterjet surgical system, the probe is supported at an acoustic node.

In addition, adjustments to the relative position between the main body member 202 and the intermediate coupling body 220 control a distance between the tip 246 of the piston 240 and the cone-shaped portion 224 of the intermediate coupling body 220, thereby controlling the efficiency of the pumping action of the piston 240 in the system 100. Adjustments to the relative position between the main body member 202 and the intermediate coupling body 220 by selectively tightening and/or loosening the coupling between the main body member 202 and the intermediate coupling body 220 using the threaded mating portions thereof.

In general therefore, it is to be appreciated that in the ultrasonically actuated high-pressure waterjet surgical system 100 of the example embodiment, the probe is attached to the actuator across a diaphragm which permits attachment of the tube and cannula in a watertight fashion. In one form, the probe is attached to the actuator via the acoustic horn. In one preferred orientation, the probe is supported at an acoustic node, wherein the acoustic horn has a weight in the shaft to accentuate the translational component of movement, and wherein the probe and actuator are attached at the sonic node of the system, such that there is no translation at the nodal plane.

Figure 3:
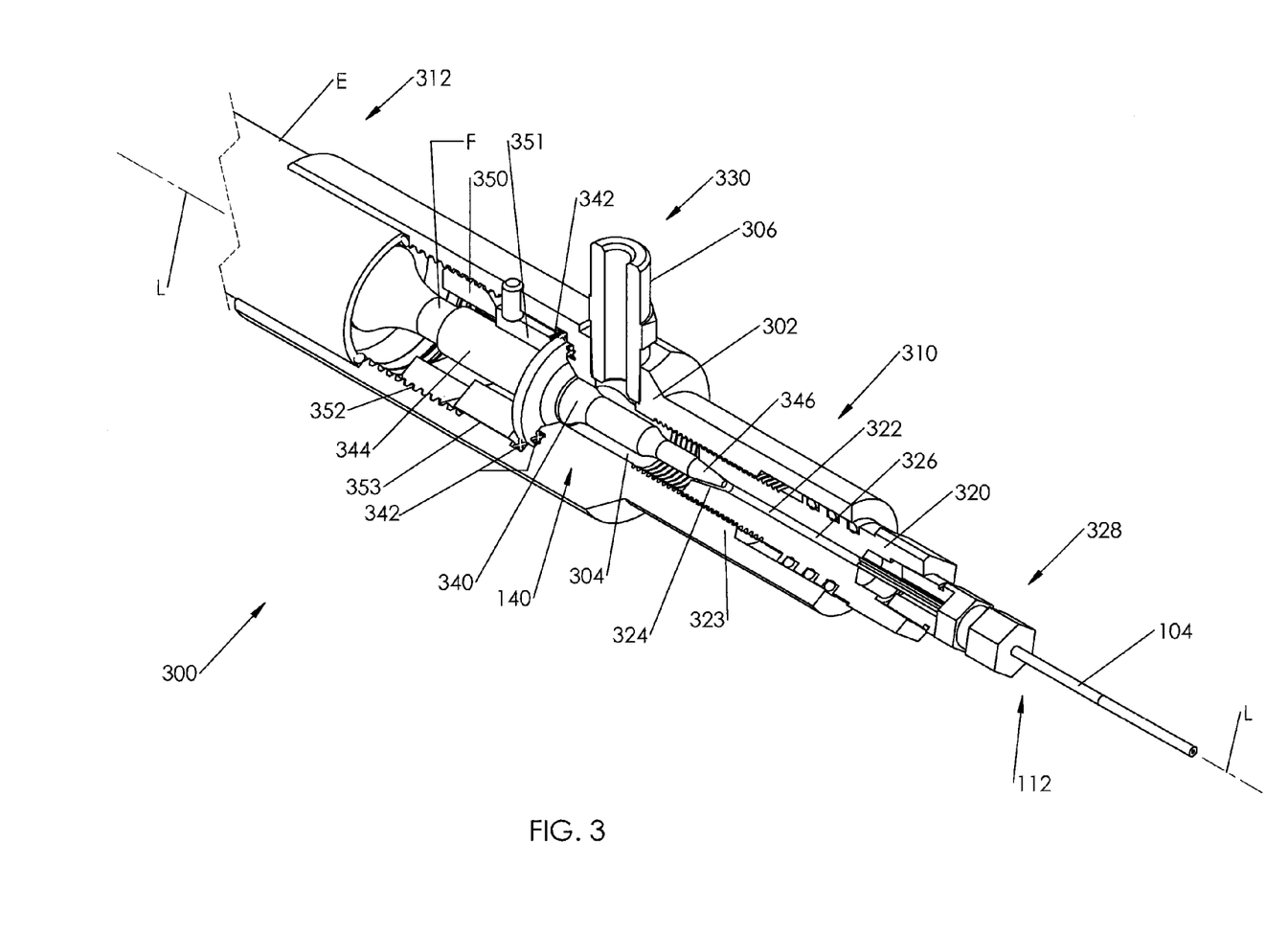
FIG. 3 is a perspective view of another embodiment of the handpiece apparatus of the subject system illustrated in partial cut-away view.

With reference to FIG. 3, an embodiment of a surgical handpiece apparatus 300 in accordance with a second example embodiment is shown in partial cut-away. The handpiece apparatus 300 of the example embodiment comprises an elongate substantially cylindrical hollow body member 302 defining a longitudinal passageway 304 therein. The passageway 304 is in fluid communication with a coupling member 306 forming a first fluid port 330 of the apparatus 300 and being configured to receive pressurized fluid from the associated source C (FIG. 1) via the associated pressurized fluid conduit D (FIG. 1).

A first or distal end 310 of the handpiece apparatus 300 is operatively coupled with the proximal end 112 of the delivery tube apparatus 104 via an intermediate coupling body 320 as shown. The intermediate coupling body 320 defines an elongate passageway 322 having a cone-shaped opening 324 on one end and a long thin portion 326 on an opposite end, wherein the cone-shaped opening 324 is shaped to correspond with a portion of a vibrating piston member 340 in a manner to be described in greater detail below. The vibrating piston member 340 comprises an acoustic horn or elongate probe and functions in the embodiment as an ultrasonic transducer apparatus. The intermediate coupling body 320 may be selectively coupled with the hollow body member 302 using any suitable means including for example by providing selectively matable threads on opposite matable surfaces of the pieces and the intermediate coupling body 320 and hollow body member 302 may be provided with grooves or the like for carrying one or more seal members such a o-rings or the like for making the connection therebetween fluid tight. In the example embodiment, the delivery tube apparatus 104 is coupled with the body member by suitable pressure compression fittings 328.

A second or proximal end 312 of the handpiece apparatus 300 is operatively coupled with a substantially cylindrical clamping members 350, 351 fastened to the hollow body member 202 using suitable threaded surfaces 352, 353. The cylindrical clamping member 350 is configured to receive the associated connection member of the associated ultrasonic generator along the longitudinal axis thereof as illustrated for selective coupling with the ultrasonic acoustic horn apparatus 140 comprising the vibrating piston member 340 and a set of biasing members 342 in the form of o-rings in the example embodiment.

In accordance with the example embodiment, the acoustic horn member 340 functions as a piston member and defines a coupling end 344 configured for selective mechanical coupling with the associated connection member F and an opposite working tip portion 346. In that way, mechanical vibrational energy from the associated ultrasonic generator E causes the member 340 to vibrate along the longitudinal axis L of the passageway 304 in turn forming pulses in the pressurized fluid within the passageway delivered from the port 330. The ultrasonic pulses are generated as the working tip portion 346 vibrates relative to the cone-shaped nozzle portion 324 of the intermediate coupling body 320. In turn, the ultrasonic pulses generated at the working tip portion 346 are directed into the delivery tube apparatus 104 for communication to the working tip 106 (FIG. 1) of the system 100 for impacting the associated tissue A or other workpiece. The nozzle is formed of any suitable material, but is in one embodiment formed of a titanium alloy. In another embodiment the nozzle is formed of ceramic, and in yet another embodiment it is formed of sapphire. Further, with regard to the mechanical vibrational energy from the associated ultrasonic generator, one preferred range of operational frequency is from about 15 kHz to about 60 kHz. However, an ultrasonic transducer frequency of about 27 kHz has been found to be particularly effective for workpieces comprising human or animal tissue.

Further in accordance with the example embodiment, the handpiece apparatus 300 may be selectively tuned by adjusting the relative position between the cylindrical clamping members 350, 351 and the main body member 302, by adjusting the relative position between the intermediate coupling body 320 and the main body member 302, or by adjusting the relative positions of both the cylindrical clamping members 350, 351 and the intermediate coupling body 320 relative to the main body member 302. More particularly, adjustments to the relative position between the cylindrical clamping members 350, 351 and the main body member 302 control a clamping force exerted by the bias members 342 on an outwardly directed flange member 348 on the piston 340. As shown, in the example embodiment, the flange member 348 is sandwiched between the bias members 342 which are in turn held in opposed contact by the relative positions along the longitudinal axis L between the cylindrical clamping members 350, 351 and the main body member 302. An amount of clamping force on the flange member 348 is used to control an amount of vibrational movement attained by the piston 340 when motivated by the associated ultrasonic generator E. Adjustments to the relative position between the cylindrical clamping members 350, 351 and the main body member 302 may be made by selectively tightening and/or loosening the cylindrical clamping members 350, 351.

In addition, adjustments to the relative position between the main body member 302 and the intermediate coupling body 320 control a distance between the tip 346 of the piston 340 and the cone-shaped portion 324 of the intermediate coupling body 320, thereby controlling the efficiency of the pumping action of the piston 340 in the system 100. Adjustments to the relative position between the main body member 302 and the intermediate coupling body 320 by selectively tightening and/or loosening the coupling between the main body member 302 and the intermediate coupling body 320 using the threaded mating portions thereof.

Figure 4:
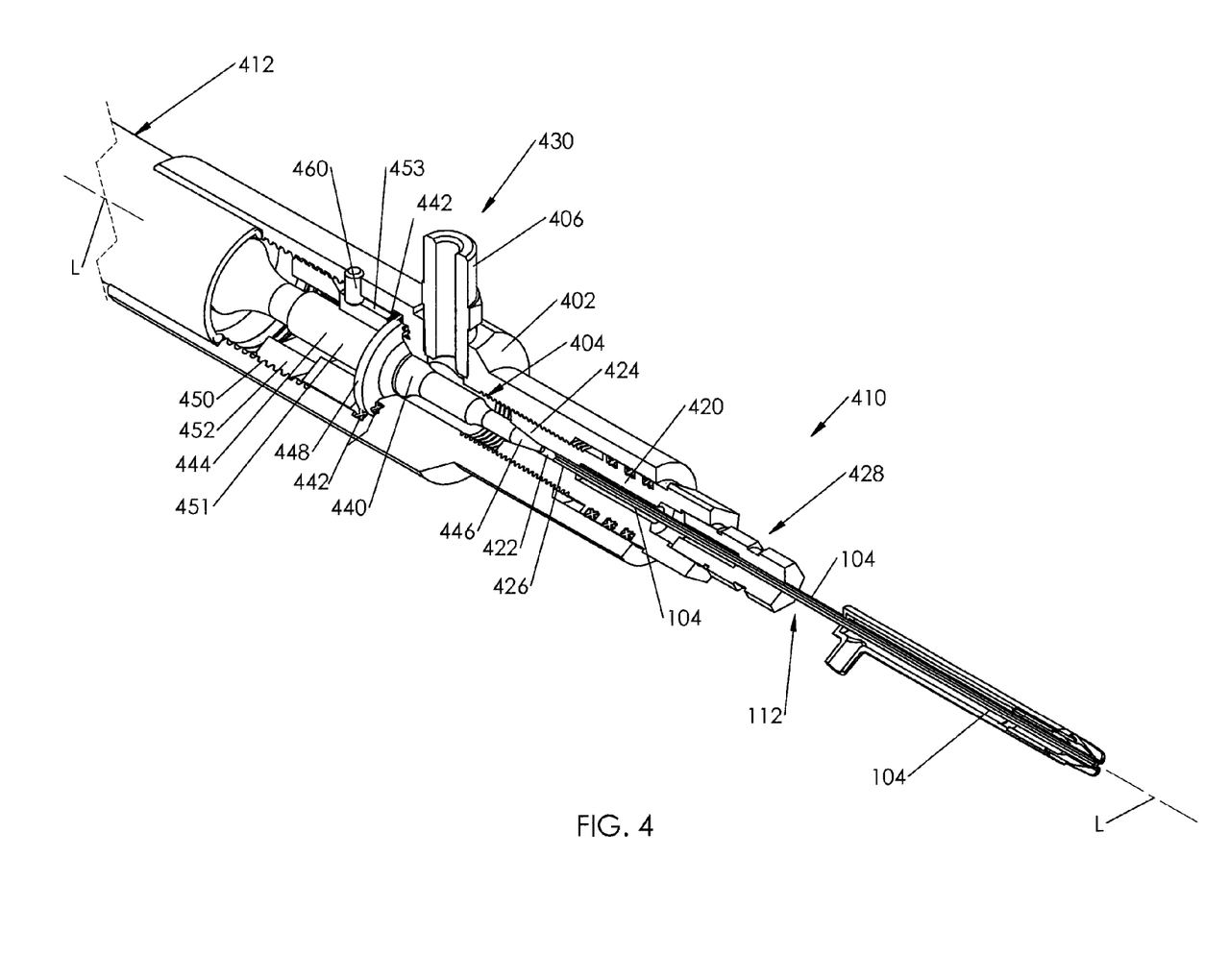
FIG. 4 is a perspective view of another embodiment of the handpiece apparatus of the subject system illustrated in partial cut-away view.

With reference to FIG. 4, an embodiment of a surgical handpiece apparatus 400 in accordance with a third example embodiment is shown in partial cut-away. The handpiece apparatus 400 of the example embodiment comprises an elongate substantially cylindrical hollow body member 402 defining a longitudinal passageway 404 therein. The passageway 404 is in fluid communication with a coupling member 406 forming a first fluid port 430 of the apparatus 400 and being configured to receive pressurized fluid from the associated source C (FIG. 1) via the associated pressurized fluid conduit D (FIG. 1).

A first or distal end 410 of the handpiece apparatus 200 is operatively coupled with the proximal end 112 of the delivery tube apparatus 104 via an intermediate coupling body 420 as shown. The intermediate coupling body 420 defines an elongate passageway 422 having a cone-shaped opening 424 on one end and a long thin portion 426 on an opposite end, wherein the cone-shaped opening 424 is shaped to correspond with a portion of a vibrating piston member 440 in a manner to be described in greater detail below. The vibrating piston member 440 comprises an acoustic horn or elongate probe and functions in the embodiment as an ultrasonic transducer apparatus. The intermediate coupling body 420 may be selectively coupled with the hollow body member 402 using any suitable means including for example by providing selectively matable threads on opposite matable surfaces of the pieces and the intermediate coupling body 420 and hollow body member 402 may be provided with grooves or the like for carrying one or more seal members such a o-rings or the like for making the connection therebetween fluid tight. In the example embodiment, the delivery tube apparatus 104 is coupled with the body member by suitable pressure compression fittings 428.

A second or proximal end 412 of the handpiece apparatus 400 is operatively coupled with substantially cylindrical clamping members 450, 451 fastened to the hollow body member 402 using suitable opposed threaded surfaces or interfaces 452, 453. The cylindrical clamping member 250 is configured to receive the associated connection member of the associated ultrasonic generator along the longitudinal axis thereof as illustrated for selective coupling with the ultrasonic acoustic horn apparatus 140 comprising the vibrating piston member 440 and a set of biasing members 442 in the form of o-rings in the example embodiment.

In accordance with the example embodiment, the acoustic horn member 440 functions as a piston member 440 defines a coupling end 444 configured for selective mechanical coupling with the associated connection member F and an opposite working tip portion 446. In that way, mechanical vibrational energy from the associated ultrasonic generator E causes the member 440 to vibrate along the longitudinal axis of the passageway 404 in turn forming pulses in the pressurized fluid within the passageway delivered from the port 430. The ultrasonic pulses are generated as the working tip portion 446 vibrates relative to the cone-shaped nozzle portion 424 of the intermediate coupling body 420. In turn, the ultrasonic pulses generated at the working tip portion 446 are directed into the delivery tube apparatus 104 for communication to the working tip 106 (FIG. 1) of the system 100 for impacting the associated tissue A or other workpiece. The nozzle is formed of any suitable material, but is in one embodiment formed of a titanium alloy. In another embodiment the nozzle is formed of ceramic, and in yet another embodiment it is formed of sapphire. Further, with regard to the mechanical vibrational energy from the associated ultrasonic generator, one preferred range of operational frequency is from about 15 kHz to about 60 kHz. However, an ultrasonic transducer frequency of about 27 kHz has been found to be particularly effective for workpieces comprising human or animal tissue.

Further in accordance with the example embodiment, the handpiece apparatus 400 may be selectively tuned by adjusting the relative position between the cylindrical clamping members 450, 451 and the main body member 402, by adjusting the relative position between the intermediate coupling body 420 and the main body member 402, or by adjusting the relative positions of both the cylindrical clamping members 450, 451 and the intermediate coupling body 420 relative to the main body member 402. More particularly, adjustments to the relative position between the cylindrical clamping members 450, 451 and the main body member 402 control a clamping force exerted by the bias members 442 on an outwardly directed flange member 448 on the piston 440. As shown, in the example embodiment, the flange member 448 is sandwiched between the bias members 442 which are in turn held in opposed contact by the relative positions along the longitudinal axis L between the cylindrical clamping members 450, 451 and the main body member 402. An amount of clamping force on the flange member 448 is used to control an amount of vibrational movement attained by the piston 440 when motivated by the associated ultrasonic generator E. Adjustments to the relative position between the cylindrical clamping members 450, 451 and the main body member 402 may be made by selectively tightening and/or loosening the clamping members 450, 451. In addition, to help prevent relative movement, a set pin 460 is provided for selectively pinning the cylindrical clamping member 451 in place relative to the main body member 402.

In addition, adjustments to the relative position between the main body member 402 and the intermediate coupling body 420 control a distance between the tip 446 of the piston 440 and the cone-shaped portion 424 of the intermediate coupling body 420, thereby controlling the efficiency of the pumping action of the piston 440 in the system 100. Adjustments to the relative position between the main body member 402 and the intermediate coupling body 420 by selectively tightening and/or loosening the coupling between the main body member 402 and the intermediate coupling body 420 using the threaded mating portions thereof.

Overall, therefore, the subject pulsated fluidjet system 100 comprises an ultrasonic transducer; a probe; a pressure tube which terminates in a nozzle; an aspirator cannula; and, wherein the handpiece permits the conversion of electrical energy into ultrasonic vibrations at the tip of the probe within the cannula, interrupting the flow of the water jet as it exits the nozzle, delivering a pulsated or interrupted jet which is used for dissociation of the target tissue. The cannula can be introduced into a surgical wound, delivering a pulsed stream of fluid to the tissue, resulting in dissociation into cells, nonviable cellular debris, and an emulsion of tissue, permitting efficient aspiration for harvesting or removal. The associated ultrasonic signal generator is provided for delivery of high-frequency pulsed current to the handpiece transducer, to convert electrical energy into ultrasonic vibrations which are used to vibrate the probe. The associated pressurized fluid source, is in the form of a closed-circuit which can be sterilized, attached to high pressure pump, to permit delivery of high-pressure fluid to the nozzle and probe tip. The associated suction aspirator system is provided for retrieval of the dissociated tissue. The electronic control unit of the subject pulsated fluidjet system 100 is configured for permitting the operator to control the action of the ultrasonic probe, the associated high pressure fluid source, and the associated suction device.

Figure 5:
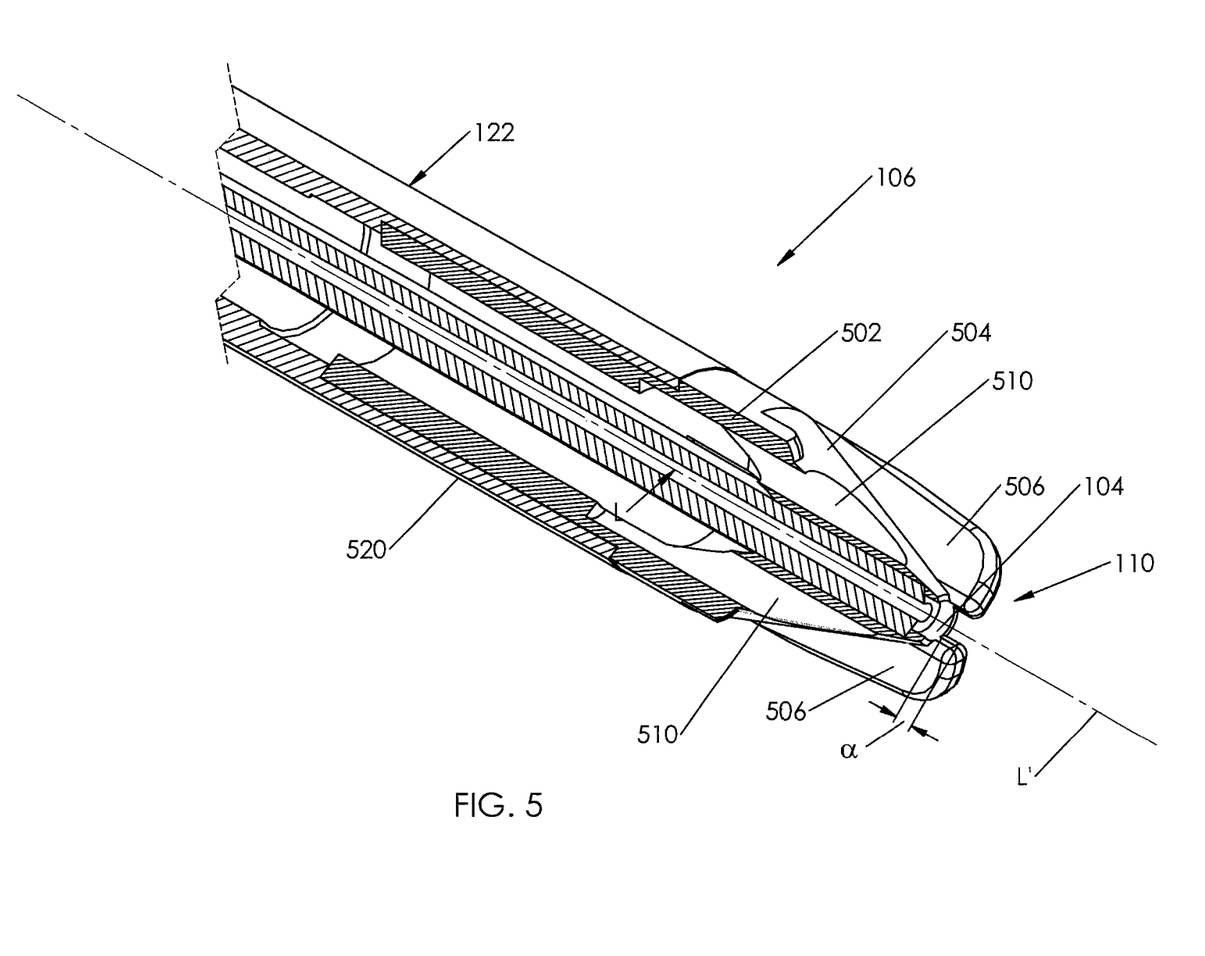
FIG. 5 is a perspective view of a distal tip portion of an embodiment of the working tip portion of the subject system illustrated in an enlarged partial cut-away view.

With reference next to FIG. 5, the working tip 106 in accordance with the example embodiment is shown in partial cut-away wherein the delivery tube apparatus 104 is surrounded by the cannula apparatus 122 in this portion of the probe. As indicated, in the embodiment, the suction aspirator apparatus 120 (FIG. 1) comprises the cannula apparatus 122 which collectively are in turn operatively connected with the associated collector device B. Overall, the suction aspirator apparatus 120 is provided in the embodiment for removal of material from the workpiece A in areas thereof impacted by the pulsating liquid jet emitted from the distal end 110 of the delivery tube apparatus.

The example tip is particularly well suited for use in surgical applications and more specifically to applications using ultrasonically pulsated fluid jet surgical devices for enhanced tissue harvesting suitable for both ablative therapy and for collection of cellular materials such as for regenerative medicine or other purposes. In this regard, the tip 106 comprises a nose member 502 preferably formed of stainless steel or titanium and defining a set of aspiration holes 510 (only one shown in the Figure) disposed in a tapered region 504 of the nose member 502. In the example embodiment shown, three (3) aspiration holes 510 are arranged in an equally spaced apart relationship (120°). Further, interposed between the spaced apart aspiration holes 510 are a set of radially extending spacer members 506. In the embodiment illustrated, the of spacer members 506 extend radially relative to the tapered region 504 of the nose member 502 as shown. In addition, preferably, the spacer members 506 extend axially or longitudinally along the axis L' for a predetermined distance d beyond the distal end of the delivery tube apparatus 104. In the example embodiment, the distance α is about 2-10 mm.

It is to be appreciated that while a set of three (3) aspiration holes 510 and a corresponding set of (3) spacer members 506 are illustrated, any combination of holes and spacer members may be used as necessary or desired to perform the functions of the holes and spacer members wherein the spacer members ensure a selected distance between the tapered region 504 and the target workpiece A and the holes provide a fluid communication port for removal of material and other tissue from the area adjacent the tip portion. In the embodiment, the aspiration holes 510 are in fluid communication with a corresponding set of passageways 520 extending longitudinally along the axis L' in the cannula apparatus 122. The set of passageways 520 within the cannula apparatus 122 are in turn in fluid communication with suction tube 124 (FIG. 1) which is in turn coupled with the associated vacuum collector device B. In this way, the ablated and or disassociated tissue is efficiently removed from the area adjacent the tip portion and collected in the associated collection device B without damage to the harvested tissue.

In one example embodiment of the ultrasonically actuated high-pressure waterjet surgical system, the probe terminates in a conical tip which corresponds to the shape of the nozzle.

In one example embodiment of the ultrasonically actuated high-pressure waterjet surgical system, the probe is connected to the transducer by a threaded rod.

In one example embodiment of the ultrasonically actuated high-pressure waterjet surgical system, the probe is connected to the transducer by an acoustic horn.

In one example embodiment of the ultrasonically actuated high-pressure waterjet surgical system, the acoustic horn is a solid member.

In one example embodiment of the ultrasonically actuated high-pressure waterjet surgical system, the acoustic horn is a hollow member with a stepped design (2 stage horn).

In one example embodiment of the ultrasonically actuated high-pressure waterjet surgical system, the acoustic horn can be made of duralumin to increase transmutation ratio.

In one example embodiment of the ultrasonically actuated high-pressure waterjet surgical system, the probe is attached to the actuator across a diaphragm which permits attachment of the tube and cannula in a watertight fashion.

In one example embodiment of the ultrasonically actuated high-pressure waterjet surgical system, the probe is attached to the actuator via the acoustic horn.

In one example embodiment of the ultrasonically actuated high-pressure waterjet surgical system, the probe is supported at an acoustic node.

In one example embodiment of the ultrasonically actuated high-pressure waterjet surgical system, the acoustic horn has a weight in the shaft to accentuate the translational component of movement.

In one example embodiment of the ultrasonically actuated high-pressure waterjet surgical system, the probe and actuator are attached at the sonic node of the system, such that there is no translation at the nodal plane.

In one example embodiment of the ultrasonically actuated high-pressure waterjet surgical system, the probe may be a straight rod or a stepped rod, or a cone.

In one example embodiment of the ultrasonically actuated high-pressure waterjet surgical system, the probe is made of titanium alloy.

In one example embodiment of the ultrasonically actuated high-pressure waterjet surgical system, the probe is isolated from the diaphragm with an O-ring seal of sufficient hardness to form a watertight seal.

In one example embodiment of the ultrasonically actuated high-pressure waterjet surgical system, the probe is subjected to ultrasonic waves by its attachment to the transducer, resulting in an intermittent interruption of the water jet.

In one example embodiment of the ultrasonically actuated high-pressure waterjet surgical system, the nozzle orifice shape enhances the impact pressure of the interrupted fluid jet stream.

In one example embodiment of the ultrasonically actuated high-pressure waterjet surgical system, the nozzle is titanium alloy.

In one example embodiment of the ultrasonically actuated high-pressure waterjet surgical system, the nozzle is ceramic.

In one example embodiment of the ultrasonically actuated high-pressure waterjet surgical system, the nozzle is sapphire.

In one example embodiment of the ultrasonically actuated high-pressure waterjet surgical system, the handpiece includes a touch pad which controls the device.

In one example embodiment of the ultrasonically actuated high-pressure waterjet surgical system, the touch pad includes a start/stop switch for the ultrasonic transducer.

In one example embodiment of the ultrasonically actuated high-pressure waterjet surgical system, the touch pad controls an input device for altering the amplitude of said ultrasonic vibrations.

In one example embodiment of the ultrasonically actuated high-pressure waterjet surgical system, the handpiece is further attached to the ultrasonic generator via a control cable.

In one example embodiment of the ultrasonically actuated high-pressure waterjet surgical system, the handpiece includes input devices for generating start and stop signals for the fluid jet control valve.

In one example embodiment of the ultrasonically actuated high-pressure waterjet surgical system, the handpiece includes input devices for generating start and stop signals for the fluid jet pump.

In one example embodiment of the ultrasonically actuated high-pressure waterjet surgical system, the handpiece includes input devices for generating start and stop signals for suction aspirator.

In one example embodiment of the ultrasonically actuated high-pressure waterjet surgical system, a footpedal control unit duplicates the functions of the handpiece includes input devices for the fluid jet, ultrasonic transducer, control valve, pump, and suction aspirator.

In one example embodiment of the ultrasonically actuated high-pressure waterjet surgical system, the ultrasonic generator includes a display for amplitude, a control for amplitude of the vibrations, an on/off switch for both power and the ultrasonic generator, and a connector for the control cable to connect the generator to the handpiece and footpedal control units.

In one example embodiment of the ultrasonically actuated high-pressure waterjet surgical system, the aspirator includes an on/off switch, a start/stop touch for the aspiration, a vacuum gauge, and an interface to provide aspiration via a sterile circuit to the surgical handpiece (either the waterjet handpiece or a separate aspirator handpiece).

In one example embodiment of the ultrasonically actuated high-pressure waterjet surgical system, the high pressure fluid source includes an on/off switch, a fluid control valve, an interface connection to provide control of pressure, rate of flow, flow meter, pressure meter, and a connector to attach the fluid source to the handpiece.

In one example embodiment of the ultrasonically actuated high-pressure waterjet surgical system, the ultrasonic transducer has a frequency from about 15 kHz to about 60 kHz.

In one example embodiment of the ultrasonically actuated high-pressure waterjet surgical system, the ultrasonic transducer has a frequency of about 27 kHz.

In one example embodiment of the ultrasonically actuated high-pressure waterjet surgical system, the high pressure fluid source includes a pump.

In one example embodiment of the ultrasonically actuated high-pressure waterjet surgical system, the high pressure fluid source interfaces with a closed loop tubing and pressure transmission system to permit delivery of sterile high pressure fluid to the handpiece.

In one example embodiment of the ultrasonically actuated high-pressure waterjet surgical system, the suction aspirator interfaces with a closed loop tubing and vacuum transmission system to permit delivery of sterile collection of tissues and cells from the treated tissues.

In one example embodiment of the ultrasonically actuated high-pressure waterjet surgical system, the suction aspirator of claim 17 includes a filter element in a sterilizable container.

In one example embodiment of the ultrasonically actuated high-pressure waterjet surgical system, the ultrasonic transducer contains a piezoelectric crystal or ceramic.

In one example embodiment of the ultrasonically actuated high-pressure waterjet surgical system, the ultrasonic transducer contains a piezomagnetic element.

In one example embodiment of the ultrasonically actuated high-pressure waterjet surgical system, the ultrasonic transducer contains a piezomagnetic element made of a megnetostrictive material.

In one example embodiment of the ultrasonically actuated high-pressure waterjet surgical system, the ultrasonic transducer contains a piezomagnetic element wherein the magnetostricive material is Terfenol.

In one example embodiment of the ultrasonically actuated high-pressure waterjet surgical system, the piezomagnetic element is comprised of a core and a magnet in a nested cylindrical arrangement.

In one example embodiment of the ultrasonically actuated high-pressure waterjet surgical system, the ultrasonic transducer has a frequency from about 15 kHz to about 60 kHz.

In one example embodiment of the ultrasonically actuated high-pressure waterjet surgical system, the ultrasonic transducer has a frequency of about 27 kHz.

In one example embodiment of the ultrasonically actuated high-pressure waterjet surgical system, the ultrasonic transducer has a frequency from about 15 kHz to about 60 kHz.

In one example embodiment of the ultrasonically actuated high-pressure waterjet surgical system, the ultrasonic transducer has a frequency of about 27 kHz.

In one example embodiment of the ultrasonically actuated high-pressure waterjet surgical system, the ultrasonic transducer has a frequency from about 15 kHz to about 60 kHz.

In one example embodiment of the ultrasonically actuated high-pressure waterjet surgical system, the generator, aspirator and pump are attached to a wheeled cart.

In one example embodiment of the ultrasonically actuated high-pressure waterjet surgical system, the electric control unit comprises manually controllable switches, which permit surgeon to control each of the features of the device.

In one example embodiment of the ultrasonically actuated high-pressure waterjet surgical system, the aspirator includes a closed tubing system and canister configured to collect matter removed from the surgical site.

In one example embodiment of the ultrasonically actuated high-pressure waterjet surgical system, the aspirator includes a filter located downstream of the canister.

Figure 6:
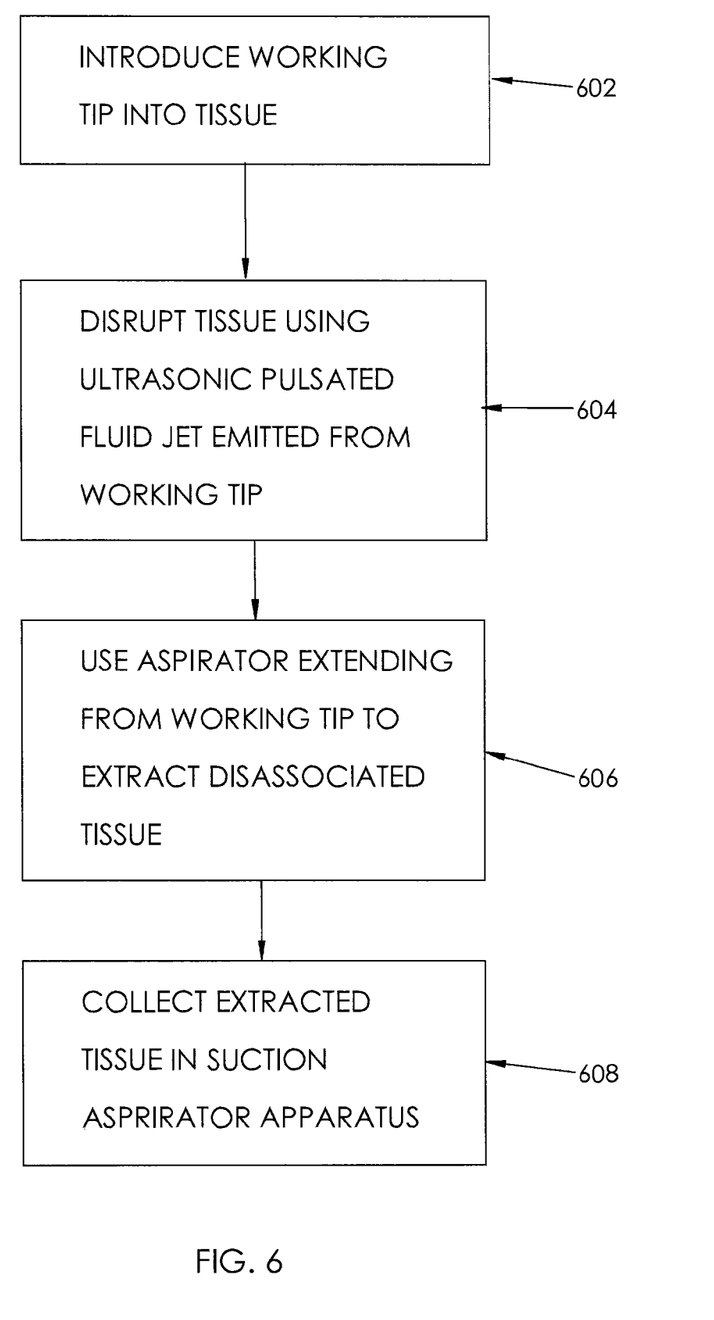
FIG. 6 is a flow chart illustrating a method of using the system of the example embodiments of the subject system shown in FIGS. 1-5.

A method 600 of using the system of the example embodiment is shown in FIG. 6, wherein an example surgical technique consists of creating a small skin incision in a suitable area of donor subcutaneous fat. The cannula is introduced, the pulsed fluid jet is activated, aspiration begins, and slow passes are made with the cannula in the subcutaneous plane as in conventional liposuction. The procedure is terminated once adequate volume has been aspirated to provide an adequate population of MSCs. The closed receptacle is accessed through its sterile port after filtration, loading the aqueous fraction of concentrated cells in a syringe for reinjection or combination with growth factors, carrier matrix, etc. In the Figure, the method 600 comprises, in general, introducing the working tip into a target tissue at 602. This may be performed, for example, by creating a small skin incision in a suitable area of donor subcutaneous fat and inserting the working tip 106 and delivery tube apparatus 104 into the suitable area. In step 604, the tissue is disrupted using the ultrasonic pulsated fluid jet emitted from the working tip once the pulsed fluid jet is activated. Aspiration is used in step 606 wherein the aspirator extending from the working tip is used to extract tissue disassociated by the ultrasonic pulsed fluid jet. Thereafter, in step 608, the extracted tissue is collected in the suction aspirator apparatus 120 via the cannula apparatus 122.

In yet a further example embodiment of the present application, a method of liposuction comprises providing a ultrasonically actuated high-pressure waterjet surgical system 100 of the type described above, and disrupting adipose tissues for aesthetic or therapeutic goals using a ultrasonic waterjet surgical system.

In yet a further example embodiment of the present application, a method of stem cell harvest using said ultrasonic waterjet surgical system 100 for use in regenerative medicine, comprises: introducing a cannula of the ultrasonic waterjet surgical system into the subcutaneous or other tissue of a patient or animal to be treated, utilizing the jet to disrupt the treated tissues, and the aspirator to retrieve the dissociated tissue into the cartridge, where it can be withdrawn sterilely for reintroduction as a stem cell concentrate, mixed with growth factors or other regenerative elements prior to reintroduction, or utilized for culture of said stem cell mixture prior to reintroduction at a second surgical intervention.

What is claimed is:
1. An ultrasonically pulsated waterjet system comprising:
a handpiece apparatus comprising a handpiece body member and a cylindrical clamping member coupled with the handpiece body member, the handpiece body member having opposite distal and proximal ends and defining an elongate longitudinal passageway extending therein along a longitudinal axis, the elongate passageway forming a nozzle terminating in an elongate pressure tube exiting the handpiece body member at a distal end thereof;

a set of biasing members disposed between the cylindrical clamping member and the handpiece body member;

a fluid port comprising a coupling member configured to selectively connect the passageway of the handpiece body member with an associated source of a pressurized fluid for selectively permitting the pressurized fluid to flow into the passageway;

an elongate delivery tube apparatus extending from the distal end of the handpiece body member to a working tip portion of the delivery tube apparatus, the delivery tube apparatus defining an elongate conduit in operative fluid communication with the passageway of the handpiece body member;

an ultrasonic transducer member comprising an elongate piston member disposed in the passageway, the elongate piston member having opposite tip and coupling ends and an outwardly extending flange member arranged between the opposite tip and coupling ends, the tip end being shaped to correspond with a selected portion of the passageway, the coupling end comprising a coupling portion configured to selectively couple the ultrasonic transducer member with an associated source of ultrasonic vibrations whereby the ultrasonic vibrations cause the ultrasonic transducer member to vibrate along the longitudinal axis to periodically interrupt the pressurized fluid flow at the nozzle with the tip end thereby delivering a pulsated jet of the pressurized fluid to the delivery tube apparatus for dissociation of associated target tissue adjacent the working tip portion by the pulsated jet of the pressurized fluid impacting the associated target tissue, and a portion of the outwardly extending flange member being held between the set of biasing members for supporting the piston member relative to the handpiece body member and the cylindrical clamping member enabling the elongate piston member to vibrate in the passageway along the longitudinal axis; and, a suction aspirator apparatus comprising a cannula extending from the working tip portion along a selected length of the delivery tube apparatus, and an elongate flexible suction tube operatively coupled with an associated fluid collector, wherein the dissociated target tissue is drawn into the cannula at the working tip portion and communicated to the associated fluid collector via the elongate flexible suction tube.

2. The ultrasonically actuated high-pressure waterjet system of claim 1 wherein the elongate piston member terminates in a conical tip which corresponds to the shape of the nozzle.

3. The ultrasonically actuated high-pressure waterjet system of claim 1 wherein the elongate piston member is connected with the transducer by a threaded rod.

4. The ultrasonically actuated high-pressure waterjet system of claim 1 wherein the elongate piston member comprises an acoustic horn.

5. The ultrasonically actuated high-pressure waterjet system of claim 4 wherein the acoustic horn is a solid member.

6. The ultrasonically actuated high-pressure waterjet system of claim 4 wherein the acoustic horn is a hollow member having a stepped shape.

7. The ultrasonically actuated high-pressure waterjet system of claim 4 wherein the acoustic horn comprises duralumin.

8. The ultrasonically actuated high-pressure waterjet system of claim 4 wherein the acoustic horn comprises a shaft having a weight selected to accentuate a translational component of movement along the longitudinal axis.

9. The ultrasonically actuated high-pressure waterjet system of claim 1 wherein the elongate piston member is attached with the associated source of ultrasonic vibrations across a diaphragm which permits attachment of the elongate delivery tube and cannula in a watertight fashion.

10. The ultrasonically actuated high-pressure waterjet system of claim 1 wherein the elongate piston member is supported at an acoustic node.

11. The ultrasonically actuated high-pressure waterjet system of claim 1 wherein the elongate piston member is attached at a sonic node of the piston member, such that there is no translation at the nodal plane.

12. The ultrasonically actuated high-pressure waterjet system of claim 1 wherein the elongate piston member comprises one or more of a straight rod, a stepped rod, and/or a cone.

13. The ultrasonically actuated high-pressure waterjet system of claim 1 wherein the elongate piston member is made of titanium alloy.

14. The ultrasonically actuated high-pressure waterjet system of claim 1 wherein the elongate piston member is isolated from the handpiece body member and the cylindrical clamping member by the set of biasing members comprising an O-ring seal of sufficient hardness to form a watertight seal.

15. The ultrasonically actuated high-pressure waterjet system of claim 1 wherein the elongate piston member is subjected to ultrasonic waves by its attachment to the transducer, resulting in an intermittent interruption of the water jet.

16. The ultrasonically actuated high-pressure waterjet system of claim 1 wherein the nozzle defines an orifice having a shape that enhances an impact pressure of the interrupted fluid jet stream.

17. The ultrasonically actuated high-pressure waterjet system of claim 1 wherein the nozzle comprises titanium alloy.

18. The ultrasonically actuated high-pressure waterjet system of claim 1 wherein the nozzle comprises ceramic.

19. The ultrasonically actuated high-pressure waterjet system of claim 18 wherein the ultrasonic transducer member has a frequency from about 15 kHz to about 60 kHz.

20. The ultrasonically actuated high-pressure waterjet system of claim 18 wherein the ultrasonic transducer member has a frequency of about 27 kHz.

21. The ultrasonically actuated high-pressure waterjet system of claim 1 wherein the nozzle comprises sapphire.

22. The ultrasonically actuated high-pressure waterjet system of claim 21 wherein the ultrasonic transducer member has a frequency from about 15 kHz to about 60 kHz.

23. The ultrasonically actuated high-pressure waterjet system of claim 21 wherein the ultrasonic transducer member has a frequency of about 27 kHz.

24. The ultrasonically actuated high-pressure waterjet system of claim 1 wherein said handpiece apparatus comprises a touch pad comprising one or more manually operable switches which are selectively operable to control the system.

25. The ultrasonically actuated high-pressure waterjet system of claim 24 wherein said touch comprises a start/stop switch operable for starting/stopping the ultrasonic transducer member.

26. The ultrasonically actuated high-pressure waterjet system of claim 24 wherein said touch pad controls an input device for altering an amplitude of said ultrasonic vibrations.

27. The ultrasonically actuated high-pressure waterjet system of claim 1 wherein said handpiece apparatus is further attached to the associated source of ultrasonic vibrations via a control cable.

28. The ultrasonic waterjet system of claim 27 wherein the aspirator includes a filter located downstream of the canister.

29. The ultrasonically actuated high-pressure waterjet system of claim 1 wherein said handpiece apparatus comprises one or more input devices for generating start and stop signals for selectively actuating the ultrasonic transducer member.

30. The ultrasonically actuated high-pressure waterjet system of claim 1 wherein said handpiece apparatus comprises one or more input devices for generating start and stop signals for the pulsated jet of the pressurized fluid.

31. The ultrasonically actuated high-pressure waterjet system of claim 1 wherein said handpiece apparatus comprises one or more input devices for generating start and stop signals for the suction aspirator apparatus.

32. The ultrasonically actuated high-pressure waterjet system of claim 1 further comprising a footpedal control unit configured to duplicate one or more functions of the handpiece includes input devices for the fluid jet, the ultrasonic transducer member, control valve, pump, and the suction aspirator apparatus.

33. The ultrasonically actuated high-pressure waterjet system of claim 1 wherein the ultrasonic generator includes a display for amplitude, a control for amplitude of the vibrations, an on/off switch for both power and the ultrasonic generator, and a connector for the control cable to connect the generator to the handpiece and footpedal control units.

34. The ultrasonically actuated high-pressure waterjet system of claim 1 wherein said aspirator includes an on/off switch, a start/stop touch for the aspiration, a vacuum gauge, and an interface to provide aspiration via a sterile circuit to the surgical handpiece.

35. The ultrasonically actuated high-pressure waterjet system of claim 1 wherein said high pressure fluid source comprises an on/off switch, a fluid control valve, an interface connection to provide control of pressure, rate of flow, flow meter, pressure meter, and a connector to attach the fluid source to the handpiece.

36. The ultrasonically actuated high-pressure waterjet system of claim 1 wherein said the ultrasonic transducer member has a frequency from about 15 kHz to about 60 kHz.

37. The ultrasonically actuated high-pressure waterjet system of claim 1 wherein said the ultrasonic transducer member has a frequency of about 27 kHz.

38. The ultrasonically actuated high-pressure waterjet system of claim 1 wherein said high pressure fluid source includes a pump.

39. The ultrasonically actuated high-pressure waterjet system of claim 1 wherein said high pressure fluid source interfaces with a closed loop tubing and pressure transmission system to permit delivery of sterile high pressure fluid to the handpiece apparatus.

40. The ultrasonically actuated high-pressure waterjet system of claim 1 wherein said suction aspirator apparatus interfaces with a closed loop tubing and vacuum transmission system to permit delivery of sterile collection of tissues and cells from the treated tissues.

41. The ultrasonically actuated high-pressure waterjet system of claim 1 wherein said suction aspirator apparatus comprises a filter element in a sterilizable container.

42. The ultrasonically actuated high-pressure waterjet system of claim 1 wherein said ultrasonic transducer member comprises a piezoelectric crystal or ceramic.

43. The ultrasonically actuated high-pressure waterjet system of claim 1 wherein said ultrasonic transducer member comprises a piezomagnetic element.

44. The ultrasonically actuated high-pressure waterjet system of claim 1 wherein said ultrasonic transducer member comprises a piezomagnetic element made of a megnetostrictive material.

45. The ultrasonically actuated high-pressure waterjet system of claim 1 wherein said ultrasonic transducer member comprises a piezomagnetic element wherein the magnetostricive material is Terfenol.

46. The ultrasonically actuated high-pressure waterjet system of claim 1 wherein said ultrasonic transducer member comprises a piezomagnetic element comprising a core and a magnet in a nested cylindrical arrangement.

47. The ultrasonically actuated high-pressure waterjet system of claim 1 wherein said generator, aspirator and pump are attached to a wheeled cart.

48. The ultrasonically actuated high-pressure waterjet system of claim 1, wherein the electric control unit comprises manually controllable switches, which permit surgeon to control each of the features of the device.

49. The ultrasonic waterjet system of claim 1 wherein the aspirator includes a closed tubing system and canister configured to collect matter removed from the surgical site.

50. An ultrasonically pulsated waterjet system comprising:
a source of pressurized fluid;
a fluid collector;
a handpiece apparatus comprising a handpiece body member and a cylindrical clamping member coupled with the handpiece body member, the handpiece body member having opposite distal and proximal ends and defining an elongate longitudinal passageway extending therein along a longitudinal axis, the elongate passageway forming a nozzle terminating in an elongate pressure tube exiting the handpiece body member at a distal end thereof;
a set of biasing members disposed between the cylindrical clamping member and the handpiece body member;
a fluid port comprising a coupling member configured to selectively connect the passageway of the handpiece body member with the source of pressurized fluid for selectively permitting the pressurized fluid to flow into the passageway;
an elongate delivery tube apparatus extending from the distal end of the handpiece body member to a working tip portion of the delivery tube apparatus, the delivery tube apparatus (104) defining an elongate conduit in operative fluid communication with the passageway of the handpiece body member;
an ultrasonic transducer member comprising an elongate piston member disposed in the passageway, the elongate piston member having opposite tip and coupling ends and an outwardly extending flange member arranged between the opposite tip and coupling ends, the tip end being shaped to correspond with a cone-shaped portion of the passageway, the coupling end comprising a coupling portion configured to selectively couple the ultrasonic transducer member with an associated source of ultrasonic vibrations whereby the ultrasonic vibrations cause the ultrasonic transducer member to vibrate along the longitudinal axis to periodically interrupt the pressurized fluid flow at the nozzle with the tip end thereby delivering a pulsated jet of the pressurized fluid to the delivery tube apparatus for dissociation of associated target tissue adjacent the working tip portion by the pulsated jet of the pressurized fluid impacting the associated target tissue, and a portion of the outwardly extending flange member being held between the set of biasing members for supporting the piston member relative to the handpiece body member and the cylindrical clamping member enabling the elongate piston member to vibrate in the passageway along the longitudinal axis; and, a suction aspirator apparatus comprising a cannula extending from the working tip portion along a selected length of the delivery tube apparatus (104), and an elongate flexible suction tube operatively coupled with the fluid collector, wherein the dissociated target tissue is drawn into the cannula at the working tip portion and communicated to the associated fluid collector via the elongate flexible suction tube.

51. An ultrasonically pulsated waterjet system comprising:

a source of ultrasonic vibrations;

a handpiece apparatus comprising a handpiece body member and a cylindrical clamping member coupled with the handpiece body member, the handpiece body member having opposite distal and proximal ends and defining an elongate longitudinal passageway extending therein along a longitudinal axis, the elongate passageway forming a nozzle terminating in an elongate pressure tube exiting the handpiece body member at a distal end thereof;

a set of biasing members disposed between the cylindrical clamping member and the handpiece body member;

a fluid port comprising a coupling member configured to selectively connect the passageway of the handpiece body member with an associated source of a pressurized fluid for selectively permitting the pressurized fluid to flow into the passageway;

an elongate delivery tube apparatus extending from the distal end of the handpiece body member to a working tip portion of the delivery tube apparatus, the delivery tube apparatus defining an elongate conduit in operative fluid communication with the passageway of the handpiece body member;

an ultrasonic transducer member comprising an elongate piston member disposed in the passageway, the elongate piston member having opposite tip and coupling ends and an outwardly extending flange member arranged between the opposite tip and coupling ends, the tip end being shaped to correspond with a selected portion of the passageway, the coupling end comprising a coupling portion configured to selectively couple the ultrasonic transducer member with the source of ultrasonic vibrations, wherein the ultrasonic vibrations cause the ultrasonic transducer member to vibrate along the longitudinal axis to periodically interrupt the pressurized fluid flow at the nozzle with the tip end thereby delivering a pulsated jet of the pressurized fluid to the delivery tube apparatus for dissociation of associated target tissue adjacent the working tip portion by the pulsated jet of the pressurized fluid impacting the associated target tissue, and a portion of the outwardly extending flange member being held between the set of biasing members for supporting the piston member relative to the handpiece body member and the cylindrical clamping member enabling the elongate piston member to vibrate in the passageway along the longitudinal axis; and, a suction aspirator apparatus comprising a cannula extending from the working tip portion along a selected length of the delivery tube apparatus, and an elongate flexible suction tube operatively coupled with an associated fluid collector, wherein the dissociated target tissue is drawn into the cannula at the working tip portion and communicated to the associated fluid collector via the elongate flexible suction tube.

52. An ultrasonically pulsated waterjet system comprising:

a source of pressurized fluid;

a fluid collector;

a source of ultrasonic vibrations;

a handpiece apparatus comprising a handpiece body member and a cylindrical clamping member coupled with the handpiece body member, the handpiece body member having opposite distal and proximal ends and defining an elongate longitudinal passageway extending therein along a longitudinal axis, the elongate passageway forming a nozzle terminating in an elongate pressure tube exiting the handpiece body member at a distal end thereof;

a set of biasing members disposed between the cylindrical clamping member and the handpiece body member;

a fluid port comprising a coupling member configured to selectively connect the passageway of the handpiece body member with the source of pressurized fluid for selectively permitting the pressurized fluid to flow into the passageway;

an elongate delivery tube apparatus extending from the distal end of the handpiece body member to a working tip portion of the delivery tube apparatus, the delivery tube apparatus defining an elongate conduit in operative fluid communication with the passageway of the handpiece body member;

an ultrasonic transducer member comprising an elongate piston member disposed in the passageway, the elongate piston member having opposite tip and coupling ends and an outwardly extending flange member arranged between the opposite tip and coupling ends, the tip end being shaped to correspond with a selected portion of the passageway, the coupling end comprising a coupling portion configured to selectively couple the ultrasonic transducer member with the source of ultrasonic vibrations whereby the ultrasonic vibrations cause the ultrasonic transducer member to vibrate along the longitudinal axis to periodically interrupt the pressurized fluid flow at the nozzle with the tip end thereby delivering a pulsated jet of the pressurized fluid to the delivery tube apparatus for dissociation of associated target tissue adjacent the working tip portion by the pulsated jet of the pressurized fluid impacting the associated target tissue, and a portion of the outwardly extending flange member being held between the set of biasing members for supporting the piston member relative to the handpiece body member and the cylindrical clamping member enabling the elongate piston member to vibrate in the passageway along the longitudinal axis; and, a suction aspirator apparatus comprising a cannula extending from the working tip portion along a selected length of the delivery tube apparatus, and an elongate flexible suction tube operatively coupled with the fluid collector, wherein the dissociated target tissue is drawn into the cannula at the working tip portion and communicated to the associated fluid collector via the elongate flexible suction tube.

* * * * *